(12) United States Patent
Fleischmann

(10) Patent No.: US 9,012,714 B2
(45) Date of Patent: Apr. 21, 2015

(54) WOUND TREATMENT DEVICE

(71) Applicant: Wilhelm Fleischmann, Bietigheim-Bissingen (DE)

(72) Inventor: Wilhelm Fleischmann, Bietigheim-Bissingen (DE)

( * ) Notice: Subject to any disclaimer, the term of this patent is extended or adjusted under 35 U.S.C. 154(b) by 0 days.

(21) Appl. No.: 13/727,242

(22) Filed: Dec. 26, 2012

(65) Prior Publication Data

US 2013/0116635 A1  May 9, 2013

Related U.S. Application Data

(63) Continuation of application No. 11/816,411, filed as application No. PCT/EP2005/012621 on Nov. 25, 2005, now Pat. No. 8,376,972.

(30) Foreign Application Priority Data

Feb. 15, 2005 (DE) .................. 10 2005 007 016

(51) Int. Cl.
*A61H 1/00* (2006.01)
*A61H 1/02* (2006.01)
*A61H 5/00* (2006.01)
(Continued)

(52) U.S. Cl.
CPC . *A61F 13/00068* (2013.01); *A61F 2013/00119* (2013.01); *A61F 2013/00174* (2013.01); *A61F 2013/00412* (2013.01); *A61F 2013/00536* (2013.01); *A61F 2013/0074* (2013.01); *A61F 2013/00957* (2013.01); *A61M 1/0088* (2013.01);
(Continued)

(58) Field of Classification Search
USPC .......... 601/6, 1, 8, 9, 148; 602/41–44, 47, 53, 602/75–76; 604/176, 217, 314–317, 48, 73, 604/93.01, 133, 149, 290, 304, 313, 327, 604/328, 540, 543

See application file for complete search history.

(56) References Cited

U.S. PATENT DOCUMENTS 268,632 A 12/1882 Darforth
583,455 A 9/1948 Bush
(Continued)

FOREIGN PATENT DOCUMENTS

DE 4335432 4/1995
DE 19832634 1/2000
(Continued)

OTHER PUBLICATIONS

Keetenwirk-Praxis, "Neue Musterungsmoglichkeiten," 2: 47-48 (2001).
(Continued)

*Primary Examiner* — Thomas J Sweet
*Assistant Examiner* — Brandon L Jackson
(74) *Attorney, Agent, or Firm* — Akerman LLP; Peter A. Chiabotti

(57) ABSTRACT

A wound treatment device comprises a wound surface contacting plug and a cover for covering the wound surface and the plug, wherein said plug consists of a flat textile isolating material comprising at least one first surface layer, one second surface layer and one intermediate space arranged between said surface layers. At least the first surface layer is provided with a biocompatible surface and a structure which enables a liquid to pass and prevents a wound tissue from growing in said structure. The intermediate space is provided with isolating threads elastically holding the first surface layer and the second surface layer at a certain distance from each other.

20 Claims, 3 Drawing Sheets

(51) Int. Cl.

| | | |
|---|---|---|
| *A61H 7/00* | (2006.01) | |
| *A61H 19/00* | (2006.01) | |
| *A61F 13/00* | (2006.01) | |
| *A61F 15/00* | (2006.01) | |
| *A61M 31/00* | (2006.01) | |
| *A61M 1/06* | (2006.01) | |
| *A61M 37/00* | (2006.01) | |
| *A61M 35/00* | (2006.01) | |
| *A61M 1/00* | (2006.01) | |
| *D04B 21/16* | (2006.01) | |

(52) U.S. Cl.
CPC ......... *D04B 21/16* (2013.01); *D10B 2509/022* (2013.01); *D10B 2403/021* (2013.01)

(56) References Cited

U.S. PATENT DOCUMENTS

| | | |
|---|---|---|
| 2,450,194 A | 9/1948 | Glaser |
| 2,669,747 A | 2/1954 | Detaranto |
| 3,825,010 A | 7/1974 | McDonald |
| 3,971,384 A | 7/1976 | Hasson |
| 4,382,441 A | 5/1983 | Svedman |
| 4,430,998 A | 2/1984 | Harvey |
| 4,526,173 A | 7/1985 | Sheehan |
| 4,896,680 A | 1/1990 | Hirshowitz |
| 5,127,412 A | 7/1992 | Cosmetto et al. |
| 5,176,663 A | 1/1993 | Svedman et al. |
| 5,203,783 A | 4/1993 | Harle |
| 5,234,462 A | 8/1993 | Pavletic |
| 5,263,971 A | 11/1993 | Hirshowitz et al. |
| 5,291,887 A | 3/1994 | Stanley et al. |
| 5,441,540 A | 8/1995 | Kim |
| 5,478,340 A | 12/1995 | Kluger |
| 5,486,196 A | 1/1996 | Hirshowitz et al. |
| 5,507,775 A | 4/1996 | Ger et al. |
| 5,531,790 A | 7/1996 | Frechet et al. |
| 5,549,640 A | 8/1996 | Fontenot |
| 5,549,713 A | 8/1996 | Kim |
| 5,571,138 A | 11/1996 | Blomqvist et al. |
| 5,584,856 A | 12/1996 | Jameel et al. |
| 5,589,245 A | 12/1996 | Roell |
| 5,618,310 A | 4/1997 | Ger et al. |
| 5,636,643 A | 6/1997 | Argenta et al. |
| 5,645,081 A | 7/1997 | Argenta et al. |
| 5,653,699 A | 8/1997 | Reed et al. |
| 5,662,714 A | 9/1997 | Charvin et al. |
| 5,723,009 A | 3/1998 | Frechet et al. |
| 5,733,305 A | 3/1998 | Fleischmann |
| 5,759,193 A | 6/1998 | Burbank et al. |
| 5,807,295 A | 9/1998 | Hutcheon et al. |
| 5,814,067 A | 9/1998 | Fleischmann |
| 5,893,879 A | 4/1999 | Hirshowitz et al. |
| 5,928,231 A | 7/1999 | Klein |
| 6,010,524 A | 1/2000 | Fleischmann |
| 6,106,544 A | 8/2000 | Brazeau |
| 6,120,525 A | 9/2000 | Westcott |
| 6,142,982 A | 11/2000 | Hunt et al. |
| 6,254,624 B1 | 7/2001 | Oddsen et al. |
| 6,315,780 B1 | 11/2001 | LaLonde |
| 6,398,767 B1 | 6/2002 | Fleischmann |
| 6,471,715 B1 | 10/2002 | Weiss |
| 6,733,537 B1 | 5/2004 | Fields et al. |
| 6,755,052 B1 | 6/2004 | Sytz |
| 6,755,807 B2 | 6/2004 | Risk et al. |
| 7,208,006 B2 | 4/2007 | Fleischmann |
| 7,235,090 B2 | 6/2007 | Buckman |
| 7,520,872 B2 | 4/2009 | Biggie et al. |
| 8,092,491 B2 | 1/2012 | Fleischmann |
| 8,114,124 B2 | 2/2012 | Buckman |
| 8,430,908 B2 | 4/2013 | Fleischmann |
| 2002/0188170 A1 | 12/2002 | Santamore et al. |
| 2003/0163160 A1 | 8/2003 | O'Malley et al. |
| 2003/0176890 A1 | 9/2003 | Buckman et al. |
| 2003/0225436 A1 | 12/2003 | Fleischmann |
| 2004/0267309 A1 | 12/2004 | Garvin |
| 2005/0209574 A1 | 9/2005 | Boehringer et al. |
| 2007/0156175 A1 | 7/2007 | Weadock et al. |
| 2007/0191885 A1 | 8/2007 | Fleischmann |
| 2008/0208251 A1 | 8/2008 | Weadock et al. |
| 2008/0312685 A1 | 12/2008 | O'Malley et al. |
| 2009/0326578 A1 | 12/2009 | Ewers et al. |
| 2010/0030260 A1 | 2/2010 | Fleischmann |

FOREIGN PATENT DOCUMENTS

| | | |
|---|---|---|
| DE | 19844355 | 4/2000 |
| DE | 102 09 122 A1 | 10/2003 |
| DE | 102007011570 | 9/2008 |
| EP | 0617152 | 9/1994 |
| EP | 0880953 | 12/1998 |
| EP | 1340461 | 9/2003 |
| EP | 1131024 | 9/2004 |
| FR | 2756722 A1 | 6/1998 |
| FR | 2758711 | 7/1998 |
| GB | 2292526 | 2/1996 |
| RU | 2 021 765 C1 | 10/1994 |
| RU | 1424809 | 9/1998 |
| SU | 1412751 A1 | 7/1988 |
| SU | 1457906 | 2/1989 |
| WO | 9309727 | 5/1993 |
| WO | 95/16416 | 6/1995 |
| WO | 9526698 | 10/1995 |
| WO | 9608223 | 3/1996 |
| WO | 0018343 | 4/2000 |
| WO | 01/93771 A1 | 12/2001 |
| WO | 01/93772 A1 | 12/2001 |
| WO | 02087481 | 11/2002 |
| WO | 10/092455 | 8/2010 |

OTHER PUBLICATIONS

Wollina et al., "Spacer Fabrics—A Potential Tool in the Prevention of Chronic Wounds, " Exog Dermatol, 1: 276-278 (2002).

Hirshowitz, B. et al., "Reconstructions of the tip of the nose and ala by load cycling of the nasal skin and harnessing of extra skin," In: Plast Reconstr Surg, 77:316 (1986).

Melis, P. et al., "Primary skin closure of a large groin defect after inguinal lymphadenectomy for penile cancer . . . ," In: The Jour. of Urology, 159(1): 185-187 (1998).

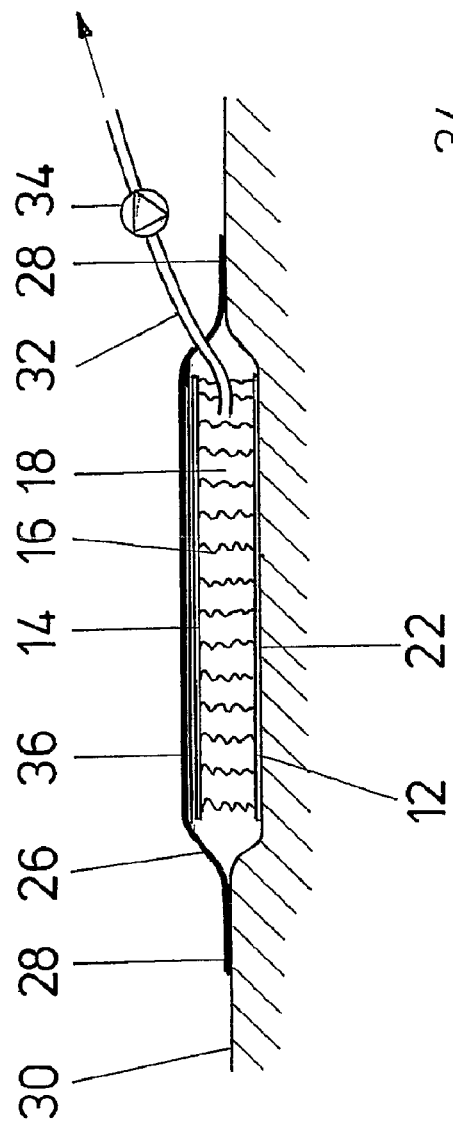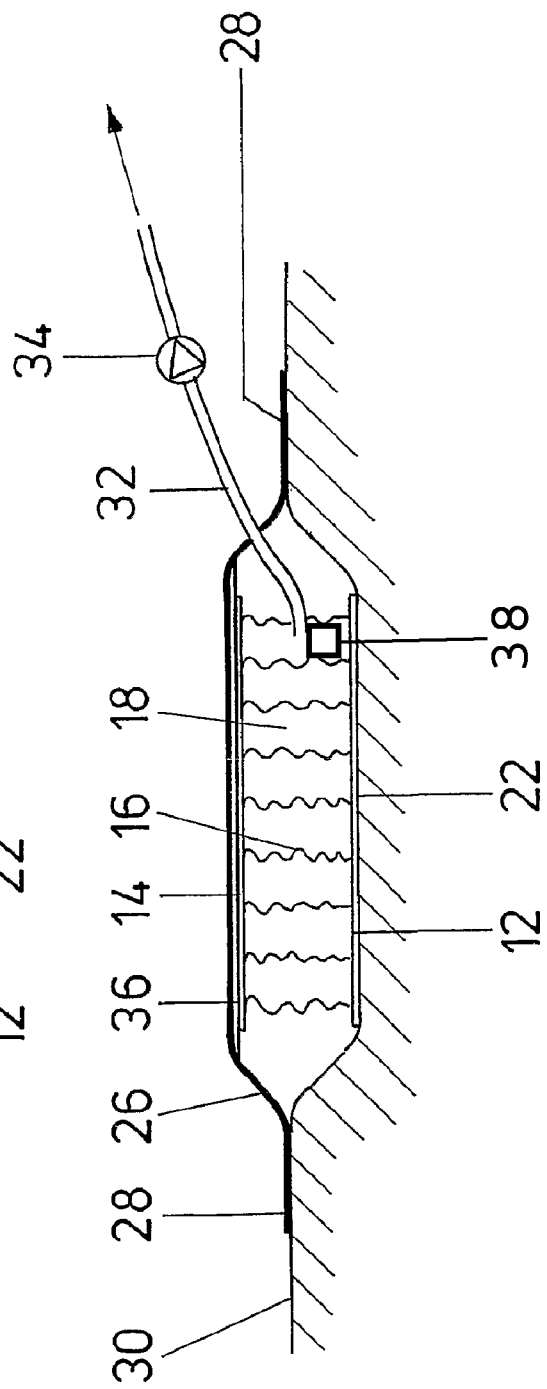
FIG 4
FIG 5

WOUND TREATMENT DEVICE

CROSS REFERENCE TO RELATED APPLICATION

This application is a continuation of, and claims priority to, U.S. Pat. No. 8,376,972, filed Aug. 15, 2007, which is the §371 National Phase of PCT/EP2005/012621, filed Nov. 25, 2005, which claims priority to German Patent Application No. 10 2005 007 016.7, filed Feb. 15, 2005, all of which are incorporated herein by reference in their entireties.

FIELD OF THE INVENTION

The invention concerns a wound treatment device.

BACKGROUND OF THE INVENTION

From EP 0 620 720 B1 it is known that a wound insert, which consists of an open-cell polymer-foam, should be placed on the wound surface. The wound surface and the wound insert are sealed over with a cover that is sealingly secured to the skin surrounding the wound surface. A vacuum can be created under the cover using a suction tube in order to vacuum tissue fluids out of the wound. The polymer-foam exhibits a relatively small pore size in order to prevent in-growth of wound tissue into the wound insert. The small-pored foam may become clogged however, for example, due to a clot, so that the vacuum effect weakens and accordingly the wound insert needs to be changed.

From U.S. Pat. No. 4,382,441 it is known that a wound insert made of small-porous foam or a textile material is placed on the wound surface and is closed off with a cover that covers the wound and is fastened around the wound surface. Hoses, which serve as supply and drain hoses, lead into the wound insert. A liquid treatment may be piped into the wound insert through these hoses, so that the treatment may come in contact with the wound surface. No vacuum is thereby produced in the wound insert. The problem of clogging may also appear in this situation.

According to EP 0 880 953 B1 the wound treatment device is improved in such a way that the supply hose and the vacuum hose may be controlled independently of one another, so that the supplied liquid treatment may be absorbed into the wound over an adjustable time period, while time intervals can be alternated where no liquid treatment is absorbed by the wound and if necessary a pressure is produced. This type of vacuum produces a pull-effect on the wound's tissue cells, thereby promoting cell growth and tissue proliferation.

SUMMARY

The task of the invention is to provide a wound treatment device which promotes the healing process.

This task is inventively solved by the wound treatment device as described herein.

Preferred embodiments and further developments of the invention are set forth in the following paragraphs.

The essential idea of the invention is to use a wound insert made of a planar or area-measured textile spacer fabric. Such spacer fabric consists of at least two surface layers in between which are located spacer filaments that hold the two surface layers elastically separated.

Such planar textile spacer fabrics are particularly produced as spacer knit fabrics. They are characterized by flexibility, compressibility and a high displacement under slight pressure (see for example Kettenwirk-Praxis 2/2001, Pages 47/48).

Spacer knit fabrics are used as upholstery in furniture for sitting and lying down, and as padding in the apparel industry.

In this context it was already proposed (Exogenous Dermatology 2002; 1, Pages 276-278) to lay patients on a textile spacer knit fabric in order to minimize the development of bedsores (decubitus ulcers).

Further, it is known from DE 198 32 643 A1 to implant a planar textile spacer material between the stomach wall and the peritoneum when treating hernea (Hernia inguinalis).

According to the invention, the planar textile spacer fabric is used as the wound insert, where at least one of the surface layers of the spacer fabric comes in contact with the surface of the wound. The surface layer of the spacer fabric that comes into contact with the wound surface has a biocompatible surface in order to guarantee tolerance with the wound tissue. Furthermore, the surface layer of the spacer fabric has a structure that on the one hand allows the passing through of a liquid, while on the other hand prevents in-growth of the wound tissue.

The wound insert allows a considerable improvement in wound treatment and wound healing. In between the surface layers is built in a large-volume interspace, where only spacer filaments are located. Tissue fluids can permeate into the interspace through the porous surface layer, and there they can be collected and stored. Where the insert is compressed by a cover, for example, by bandage material or a seal, the wound insert would exert pressure on the wound tissue, which presses or expresses the tissue fluids out of the wound tissue, which additionally supports the healing process.

Preferably, at least one hose, which is in particular constructed as the vacuum hose, comes in contact with the large-volume interspace. Tissue fluids which flow out of the wound into the interspace through the porous surface layer can be suctioned out, which makes clog formation practically impossible due to the open area space. For suctioning, it is particularly advantageous when the cover is a sealing sheet, which covers over the wound and wound insert air-tight and is sealingly attached to the skin surrounding the wound, as is known from vacuum sealing. In the same manner it is of course also possible to supply treatment liquids into the interspace through the supply hose. The treatment liquids then reach the wound through the surface layer. Optimal wound treatment is possible through the controlled supplying and vacuuming of the treatment liquid and the vacuuming of wound secretions.

The high compressibility of the textile spacer fabric in conjunction with a seal further facilitates a favorable impact on wound healing and tissue proliferation. The wound insert is placed into the wound, where vacuum is produced under the seal through the vacuum hose and with the help of a pump. The spacer material is compressed, firstly, through this vacuum-effect in opposition to the elasticity of the spacer fibers. Secondly, the vacuum-effect is also exercised on the wound tissue, whereby tractive forces act on the tissue cells. Were the suction process is terminated, for example by closing an open vacuum hose valve, the vacuum under the seal-cover would initially remain. The elastic restoring force of the spacer fabrics at this time produces a surface area pressure on the wound tissue. This pressure causes on the one hand pressure on the wound tissue. On the other hand, tissue fluid is expressed out of the intercellular space and reaches the open interspace of the spacer fabric through the porous surface layer of the spacer fabric. The alternating effect upon the cells of the tractive forces during the extraction phase and the pressure forces during the expansion phase of the spacer fabric stimulate new tissue growth particularly intensely. This is attributable, on the one hand, that the cells are cyclically deformed in directions perpendicularly to each other. Secondly, cell growth is supported because, during the pressure phase, the blood supply to the cells is reduced to ischemia, while during pressure release a reactive hyperemia and intensified blood perfusion take place. Thirdly, the tissue fluids which are located between the cells are set into motion more intensely through the pull and push effects and are thereby practically "milked" out of the tissue.

With deep wounds, the wound insert can be inserted in such a way that it lies with both surface layers against the wound surface. The elastic restoring forces of the spacer knit fabrics press apart both surface layers of the spacer knit fabrics, thereby pressing against the opposed wound surface layers. In this case the seal cover only has the task of closing off the wound in order to generate vacuum in the wound.

With shallow wounds, the wound insert is inserted onto the wound surface in such a way that only one surface layer touches the wound surface, while the opposite surface layer lies against the seal. In this case, the elastic restoring force of the spacer fabric is supported against the seal. The seal must be sufficiently tightly taut, or it must exhibit a sufficient surface rigidity.

The planar textile spacer fabric can be produced in different ways. It is particularly important that a sufficient large-volume interspace is formed through the elastic cushioning spacer filaments, and that the spacer fabric exhibits the desired elastic properties. Further, it is important that the surface layer which comes in contact with the wound be tolerated by the tissue, that the passing through of fluid be allowed and the in-growth of wound tissue be prevented. These criteria can be meet in several ways.

The substance and the dimensions of the spacer filaments are chosen according to the desired mechanical properties. That means with regard to the thickness of the spacer fabric, or, as the case may be, with regard to the space between the surface layers, and with regard to the desired elasticity. The surface layer which comes in contact with the wound can be made of a different material. Therein the spacer material can be a spacer knit fabric, into which the spacer filaments are interwoven into the surface layer forming textile ply or layer.

The surface layer can be a textile ply made of biocompatible material, whereupon the ply's slight thickness and the small mesh size ensure the desired structure.

In a different embodiment, the surface layer that is interwoven with the spacer filaments can be composed of another material, that is, chosen based on mechanical and textile-technical properties. This surface layer exhibits a structure that allows the permeation of fluids and prevents the in-growth of wound tissue. In order to assure the biocompatibility of the surface layer and the tissue tolerance toward the surface layer, the surface layer is coated with a biocompatible material. The coating may not substantially impair the structure of the surface layer.

Further, a design is possible where the surface layer includes a large-mesh support layer, in which the spacer filaments are interwoven. The support layer material can be chosen based on its mechanical and textile-mechanical properties. This support layer is covered with an upper or cover layer made of biocompatible material. This upper or cover layer can be, for instance, an adequately small-pored foam, whereby the slight layer thickness of the foam prevents a closure or clogging. The upper or cover layer can also, as the case may be, contain a substance, and may, for example, serve as a medicine carrier.

As biocompatible material, a polymer plastic is used, particularly a polyvinylalcohol.

BRIEF DESCRIPTION OF THE DRAWINGS

Below, the invention is further illustrated through drawings of the exemplary embodiments. They show.

DETAILED DESCRIPTION OF THE PREFERRED EMBODIMENTS

Figure 1:
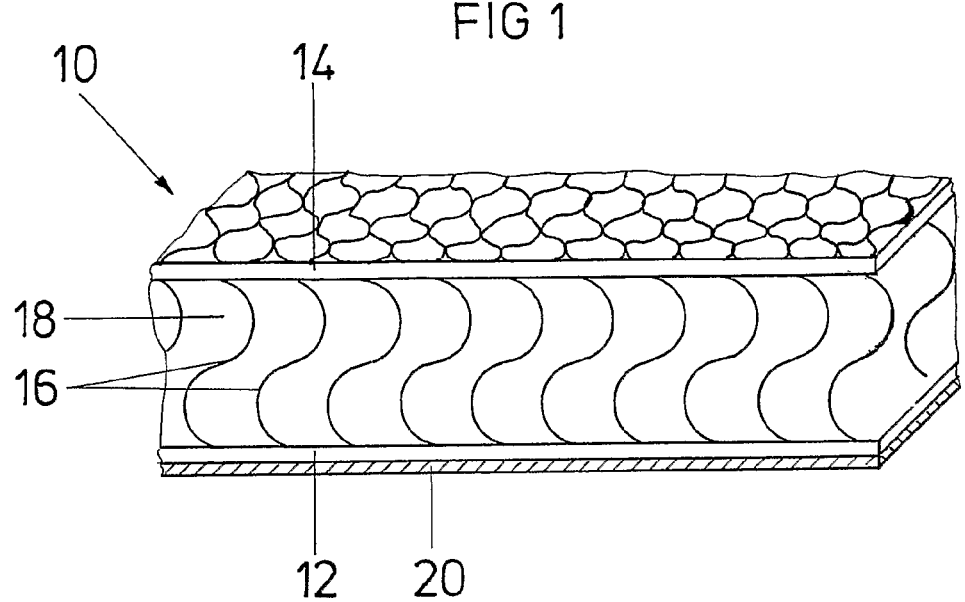
FIG. 1 schematically the composition of the wound insert,
FIG. 2 a first embodiment with compressed wound insert,
FIG. 3 this embodiment with expanding wound insert,
FIG. 4 a second embodiment for the treatment of a surface would under vacuum-seal with a compressed wound insert,
FIG. 5 the second embodiment with an expanding wound insert
FIG. 6 a third embodiment for the treatment of a deep wound with a compressed wound insert
FIG. 7 the third application example with a expanding wound insert

According to the invention, wound insert 10, whose construction is schematically illustrated in one embodiment in FIG. 1, is used. Wound insert 10 consists of a planar textile spacer fabric, and is cut into adequate size according to the respective demands of the wound that is to be treated. Should the demand arise, the wound insert can also be available in given standard dimensions. The textile spacer fabric exhibits a first surface layer 12 and a second surface layer 14. Surface layer 12 and surface layer 14 are held apart by elastic cushioning spacer filaments 16. Thus, a relatively large interspace 18 is formed between surface layer 12 and surface layer 14. In this interspace 18 are found spacer filaments 16, which exhibit a relatively large mutual separation, so that the interspace 18 in the plane of the wound insert 10 is substantially open and exhibits between the spacer filaments 16 a large free flow-through cross section. Surface layers 12 and 14 can be pressed against one another due to the elastic deformation of spacer filaments 16. Thereby, wound insert 10 is compressed and interspace 18 is diminished. It is apparent that the invention is not limited to a wound insert that exhibits only a first surface layer 12 and a second surface layer 14, but that planar textile spacer fabrics can also be used, in which are found intermediate layers between the surface layers 12 and 14, so that a multi-ply interspace 18 can be formed.

The planar textile spacer fabric of wound insert 10 be produced in conventional manner. For example, the surface layers 12 and 14 can be woven, such that the spacer filaments 16 are woven into the surface layers 12 and 14, so that a stable connection arises between surface layers 12 and 14 and spacer filaments 16. Suitable material, particularly synthetic material, is used for surface layers 12 and 14 and spacer filaments 16. The interknitting or interweaving of the filaments of surface layers 12 and 14 and of spacer filaments 16 allows in doing so the usage of different filaments for surface layers 12 and 14 and for spacer filaments 16. Spacer filaments 16 can be chosen with respect to the utilized material and with respect to the filament thickness according to the desired elastic properties. For surface layers 12 and 14, other filament strengths/sizes can be utilized, particularly small filament strengths/sizes, in order to obtain a flexible, soft surface layer 12, respectively surface layer 14. The material for surface layers 12 and 14 can also be chosen independently from the material of spacer filaments 16.

In the later described embodiment, at least one of the surface layer 12 and 14 of the wound insert 10 comes into contact with the wound surface. At least one surface layer which comes in contact with the wound surface—the first surface layer in the embodiment from FIG. 1—must fulfill, according to the invention, the following criteria. Surface layer 12 must be biocompatible, that is, it may not cause any adverse reactions in the tissue of the wound. Further, surface layer 12 must exhibit a structure which on the one hand allows liquids to pass through and on the other hand prevents the in-growth of wound tissue. These properties can be achieved in different ways. It is possible to produce surface layer 12 out of biocompatible material. Thereby, the textile ply of the surface layer 12 can be structured so that the mesh size or pore size allows the passing through of fluids, yet largely rules out the in-growth of wound tissue. It is also possible to coat the textile ply of surface layer 12 with a biocompatible material. If the textile ply already exhibits an adequate mesh size or pore size, a thin surface layer coat is sufficient, whereby the material of the coat causes the biocompatibility. The material of the textile ply of the surface layer must not in this case exhibit this biocompatibility, and can, as the case may be, be chose through other criteria, for example for the mechanical or textile-mechanical properties. If the textile ply of surface layer 12 exhibits a larger mesh size or pore size, the coat with the biocompatible material can be additionally used to reduce the mesh or pore size to such a magnitude that is required for the prevention of tissue in-growth.

In a further design, such as it is depicted in FIG. 1, surface layer 12 can be composed of a textile ply which is covered with cover layer 20. The textile ply can exhibit a relatively large mesh size, and essentially acts as the support layer for cover layer 20. In this design, there is a large freedom with respect to the construction of the spacer fabric, and especially with respect to the textile ply of surface layer 12, which serves as support layer. This freedom concerns mesh size as well as the choice of material and thread strength for the textile ply. Cover layer 20 exhibits biocompatible properties and the required structure. For cover layer 20, a thin foam film can be used, composed of an open-pore synthetic foam, for example polyvinayalcohol. Optimal biocompatibility can be achieved through the choice of synthetic material. The thickness of cover layer 20 and the pore size of the foam may be optimized to the effect that the passing through of liquids is impeded as little as possible, while the in-growth of wound tissue is reliably prevented. In place of a foam made of polymeric plastics, textile materials which exhibit the adequate structure may also be used as the cover layer 20.

Figure 2:
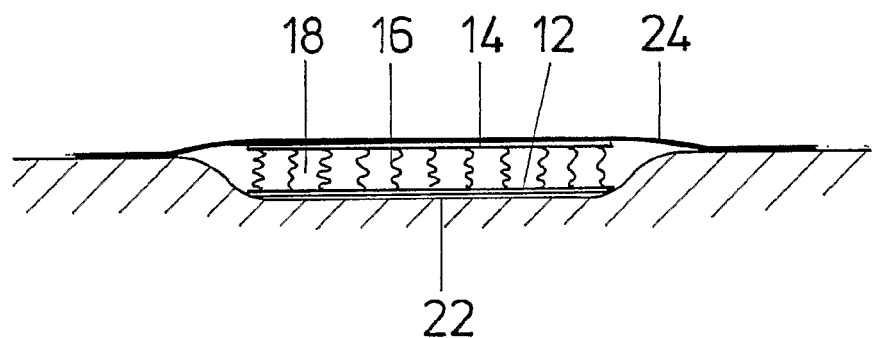
Figure 3:
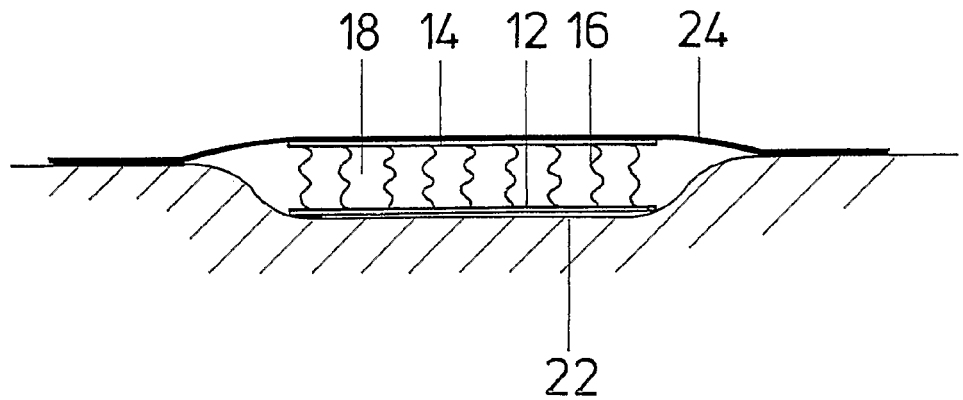

A first application possibility is illustrated in FIGS. 2 and 3. For the treatment of a shallow wound 22, wound insert 10, fitted according to the wound size, is applied. If the material of the wound insert exhibits only one surface layer 12 with the required properties for biocompatibility and structure, wound insert 10 is applied to the wound surface with surface layer 12. Afterwards, wound 22 and wound insert 10 are covered up using an appropriate wound dressing material, for example a bandage. The dressing material 24 is tautly wrapped, so that wound insert 10 is pressed flatly into wound 22. Wound insert 10 lies thereby with first surface layer 12 tightly against the wound surface, establishing a broad surface area contact with wound 22. The pressure of dressing material 24 thereby leads to a compression of wound insert 10, so that surface layers 12 and 14 are pressed against the elastic restoring force of spacer filaments 16, and interspace 18 is reduced, as is schematically illustrated in FIG. 2. The elastic restoring force of spacer filaments 16 causes pressure of the first surface layer 12 onto the tissue of wound 22, whereby dressing material 24 reinforces and supports the pressure forces. Through the pressure of wound insert 10 onto the tissue of wound 22, tissue fluids that are found in the wound tissue are expressed out of the wound tissue. This wound fluid goes through the first surface layer 12 and reaches interspace 18. Through the hereby resulting compression of the wound tissue, wound insert 10 can expand under the restoring force of spacer filaments 16, as is schematically illustrated in FIG. 3, whereby interspace 18 is enlarged and tissue fluids can be absorbed. In this manner, wound insert 10 can collect and keep away from the wound tissue a larger amount of tissue fluids, so that changing of dressing material is required less often.

Cover layer 20 can be imbued with active ingredients, for example with drugs, which promote wound healing, work against infection germination, etc. Since cover layer 20 is brought and held in tight contact with the wound tissue through the elasticity of wound insert 10, the active ingredients absorbed in cover layer 20 can be optimally applied to the wound surface.

A second embodiment is illustrated in FIGS. 4 and 5.

On a surface wound 22, wound insert 10, cut and fitted according to the wound size, is placed, where first surface layer 12, which lies on the wound surface, is constructed in the previously defined biocompatible manner and exhibits the suitable structure. Wound 22 and wound insert 10 are covered by an air-tight seal 26. Seal 26 is tightly affixed on skin 30, outside of wound 22 along a border area 28. Seal 26 can exhibit a closeable opening. The opening can be closed by, for example, an adhesive piece of paper or by a check valve that opens to the outside. After wound insert 10 is inserted and is covered with seal 26, wound insert 10 is compressed over its surface from the outside, for example by exercising pressure from the palm of the hand on seal 26. Through this compression, air can escape from the wound insert through the open opening of seal 26, or, as the case may be, through the check valve. After the compression, the opening is closed, for example, by being adhered, or, as the case may be, closed by a check valve. Wound insert 10 then lies on the wound surface, under the pressure of the expanding spacer filaments, as described above.

In a further construction, as it is illustrated in FIGS. 4 and 5, an additional hose 32 is routed, in a sealed manner, under seal 26 into interspace 18 of wound insert 10. Hose 32 is equipped with a valve 34. Hose 32 is connected to a pump or another vacuum source, so that by opening valve 34 a vacuum is produced in the wound under the seal 26. Due to the vacuum, wound insert 10 is compressed against the restoring force of the spacer filaments, as is schematically illustrated in FIG. 4. The vacuum causes thereby a pull-effect on the cells of the wound tissue. If valve 34 is closed, as is shown in FIG. 5, compressed wound insert 10 causes pressure on the wound tissue. Thereby, on the one hand pressure is exerted on the cells of the tissue, and on the other hand, tissue fluids are pressed out of the tissue and reach interspace 18 of wound insert 10 through surface layer 12. Wound insert 10 expands in the process, whereby interspace 18, increasing due to the expansion, can intake wound fluid. After an appropriate time frame, valve 34 can be opened again so that tissue fluids can be vacuumed out of interspace 18 through hose 32 and vacuum can be produced again under seal 26. This process can be repeated cyclically, so that there is an alternation between the pull-effect on the cells during the vacuum cycle and the pressure-effect on the cells during the expansion of wound insert 10, thereby promoting cell proliferation.

In this application, wound insert 10 is supported during the expansion against wound covering seal 26. In the case that this supporting effect of the seal is insufficient, seal 26 can be strengthened through a reinforcing insert 36. Further, a pressure sensor or tension sensor 38 can be placed in the wound insert, particularly in interspace 18 and/or the inner end of hose 32, in order to measure the pressure under seal 26 and in order to control the vacuum and expansion cycles according to the corresponding pressure conditions. Alternatively, an expansion sensor can also be fitted or introduced into wound insert 10, so that the distance between surface layers 12 and 14, that is, the mass of compression or expansion, can be measured in order to appropriately direct the treatment cycle.

Figure 6:
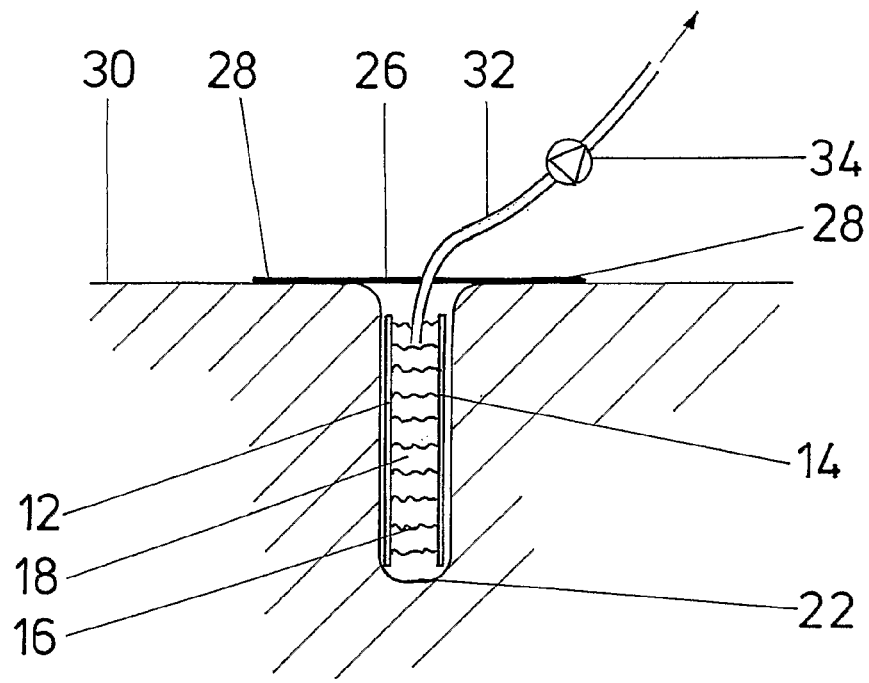
Figure 7:
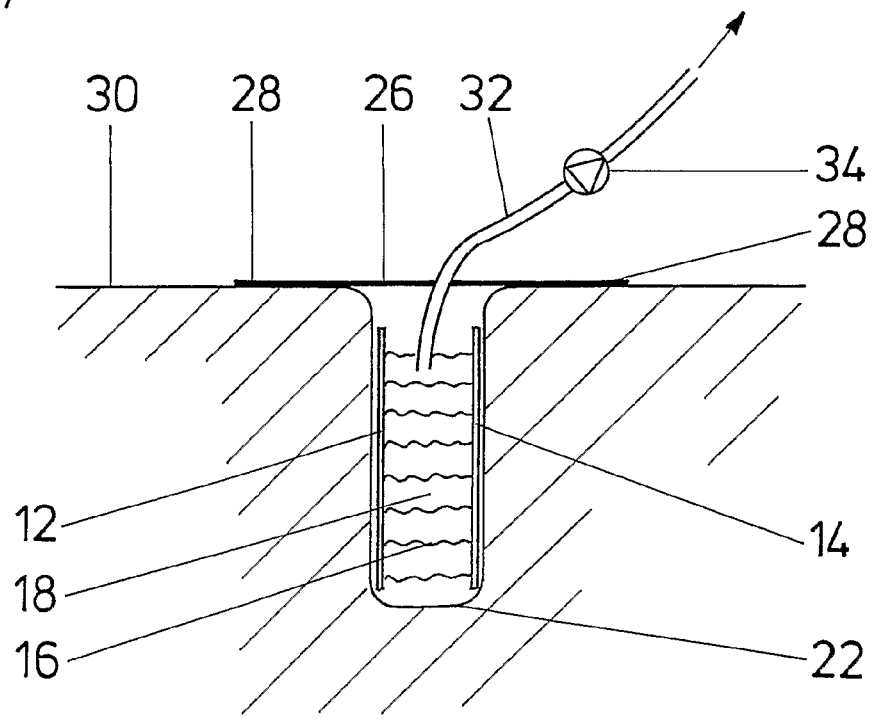

In FIGS. 6 and 7 is illustrated a further application possibility for the treatment of deep wounds.

In this application, wound insert 10, fitted according to the wound size, is placed inside a deep wound pocket 22. Wound insert 10 lies hereby with both surface layers 12 and 14 respectively against the opposite-lying surfaces of wound 22. Accordingly, in this application, surface layers 12 and 14 must be biocompatible in the afore explained manner, and must be constructed with the required structure.

After the placement of wound insert 10 into wound 22, wound 22 is closed off air-tightly using seal 26. Hose 32 with valve 34 is sealed under seal 26 and lead into wound insert 10. If a vacuum is applied through hose 32 by open valve 34, a vacuum arises in wound 22. The opposite-lying wound borders are pulled together, and wound insert 10 is compressed against the force of spacer filaments 16, as is illustrated in FIG. 6. Thereby, a pull-effect is exerted on the cells of the wound tissue. If valve 34 is closed off, the compressed wound insert 10 exerts pressure on the opposite-lying wound surfaces. Thereby, pressure is exerted on the cells of the wound tissue and tissue fluids are squeezed out and drawn into expanding interspace 18. Wound insert 10 is hereby supported against the opposite-laying wound surfaces.

In the embodiment of FIGS. 4 through 7, an instillation treatment may be carried out in an advantageous manner. Hereunto, a treatment liquid can be introduced through hose 32 or through another supply hose that is led under seal 26. Thereby, other countless treatment possibilities arise. Treatment fluid can be introduced to interspace 18, and can be brought to the wound surface through the porous structure of surface layer 12, or surface layers 12 and 14. This treatment liquid and the secreted wound liquid can in turn be vacuumed out through hose 32. By this treatment, wound insert 10 must not be compressed, or at least only be so compressed as to allow surface layer 12 or 14 deep contact with the wound surface. The large-volume open interspace 18 warrants thereby that the treatment liquid is unrestrictedly applied over the entire wound surface, and that an unhindered vacuuming-out is possible, without any danger of closure or clotting, or sticking together due to formation of coagulum or the like. Further, this installation can be combined with vacuum production in the afore described manner. Here, in controlled time intervals, treatment liquid can be applied to the wound surface, vacuum can be produced in the wound, and pressure can be exerted on the wound tissue through expanding wound insert 10.

REFERENCE NUMBER LIST 10 wound insert
12 first surface layer
14 second surface layer
16 spacer filaments
18 interspace
20 cover layer
22 wound
24 bandaging material
26 seal
28 border area
30 skin
32 hose
34 valve
36 reinforcing insert

What is claimed:

1. A wound treatment device, comprising:
    a wound insert that is insertable entirely with a wound;
    a cover for covering the wound surface and wound insert, the cover being a seal that is sealingly affixable to skin surrounding the wound; and
    a vacuum hose introducible air-tight under the seal, wherein the vacuum hose has a diameter;
    wherein the wound insert includes a planar textile spacer material and comprises:
        a first surface layer in contact with a first surface of the wound, the first surface layer exhibiting a biocompatible surface and a structure that allows the passing through of fluid and prevents in-growth of wound tissue;
        a second surface layer in contact with a second surface of the wound, the second surface layer also exhibiting the biocompatible surface and the structure that allows the passing through of fluid and prevents in-growth of wound tissue;
        an interspace between the first surface layer and the second surface layer and defining a substantially open space to receive the vacuum hose, wherein the substantially open space has a height between the first surface layer and the second surface layer that is at least greater than the diameter of the vacuum hose;
        spacer filaments located in the interspace that hold the first surface layer and the second surface layer elastically apart with an elastic restoring force, wherein the first surface layer and the second surface layer are compressed, by a vacuum force provided by the vacuum hose, against the elastic restoring force of the spacer filaments in order to reduce the interspace and wherein the first surface layer and second surface layer expand, when the vacuum force is no longer provided by the vacuum hose, in opposite directions under the elastic restoring force of the spacer filaments in order to enlarge the interspace and to exert pressure on the wound expelling wound tissue fluids that collect in the interspace; and
        wherein the vacuum hose communicates with the interspace to provide the vacuum force.

2. The wound treatment device according to claim 1, wherein spacer filaments are an elastic material that forces apart the first and second surface layers and the first surface layer comprises a biocompatible material.

3. The wound treatment device according to claim 2, wherein the first surface layer comprises a thin textile ply and small mesh size of threads of biocompatible material, into which spacer filaments are interwoven.

4. The wound treatment device according to claim 2, wherein the biocompatible material is a polymeric plastic.

5. The wound treatment device according to claim 2, wherein the biocompatible material is a polyvinyl alcohol.

6. The wound treatment device according to claim 1, wherein the first surface layer is coated with a cover layer made of a biocompatible material.

7. The wound treatment device according to claim 6, wherein the spacer filaments are interwoven into the first surface layer, and the first surface layer provides a support for the cover layer.

8. The wound treatment device according to claim 6, wherein the cover layer comprises a foam material.

9. The wound treatment device according to claim 6, wherein the cover layer comprises a small-pored textile material.

10. The wound treatment device according to claim 1, wherein the vacuum hose is controllable to open and close for vacuuming and for supplying.

11. The wound treatment device according to claim 10, wherein the vacuum hose is controllable based on pressure in the wound.

12. The wound treatment device according to claim 11, further comprising a pressure sensor located in the wound insert.

13. The wound treatment device according to claim 11, further comprising a tension sensor located in the wound insert.

14. The wound treatment device according to claim 10, wherein the vacuum hose is controllable at predetermined time intervals.

15. The wound treatment device according to claim 1, wherein the first surface layer is covered with a biocompatible material.

16. The wound treatment device according to claim 1, wherein the cover is a bandaging material.

17. The wound treatment device according to claim 1, further comprising a supply hose for supplying liquid treatment agents.

18. The wound treatment device according to claim 1, wherein the cover layer contains an active ingredient for wound application.

19. A wound treatment device, comprising:
   a wound surface cover, the wound surface cover being a seal that is sealingly affixable to skin surrounding a wound, the wound surface cover including a closeable valve that causes the seal to be air-tight when the closeable valve is closed;
   a vacuum hose introducible air-tight under the seal, wherein the vacuum hose has a diameter; and
   a wound insert that comes in contact with a wound surface, the wound insert comprising:
      a first surface layer, wherein the first surface layer has a biocompatible surface and a structure that allows the passing through of fluid;
      a second surface layer;
      an interspace between the first surface layer and the second surface layer and defining a substantially open space to receive the vacuum hose, wherein the substantially open space has a height between the first surface layer and the second surface layer that is at least greater than the diameter of the vacuum hose;
      elastic elements located in the interspace that hold the first surface layer and the second surface layer elastically apart with an elastic restoring force, wherein the first surface layer and the second surface layer are compressed, by a vacuum force provided by the vacuum hose, against the elastic restoring force of the elastic elements in order to reduce the interspace and wherein the first surface layer and second surface layer expand, when the vacuum force is no longer provided by the vacuum hose, in opposite directions under the elastic restoring force of the elastic elements in order to enlarge the interspace and to exert pressure on the wound expelling wound tissue fluids that collect in the interspace; and
      wherein the vacuum hose communicates with the interspace to provide the vacuum force.

20. The wound treatment device according to claim 19, further comprising:
   a pressure sensor located in the wound insert, and
   wherein the vacuum hose is controllable based on pressure in the wound.

* * * * *